(12) United States Patent
Hinatsu et al.

(10) Patent No.: US 11,755,710 B2
(45) Date of Patent: Sep. 12, 2023

(54) BIOMETRIC AUTHENTICATION DEVICE, BIOMETRIC AUTHENTICATION METHOD, AND COMPUTER READABLE MEDIUM

(71) Applicant: Mitsubishi Electric Corporation, Tokyo (JP)

(72) Inventors: Shun Hinatsu, Tokyo (JP); Daisuke Suzuki, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 17/742,156

(22) Filed: May 11, 2022

(65) Prior Publication Data

US 2022/0269765 A1  Aug. 25, 2022

Related U.S. Application Data

(63) Continuation of application No. PCT/JP2020/000295, filed on Jan. 8, 2020.

(51) Int. Cl.
*G06K 9/62* (2022.01)
*G06F 21/32* (2013.01)
(Continued)

(52) U.S. Cl.
CPC ............ *G06F 21/32* (2013.01); *A61B 5/0205* (2013.01); *A61B 5/02433* (2013.01);
(Continued)

(58) Field of Classification Search
CPC .... G06V 40/15; A61B 5/0205; A61B 5/0816; A61B 5/02116; A61B 5/087–5/0878; A61B 5/024–5/0255
See application file for complete search history.

(56) References Cited

U.S. PATENT DOCUMENTS 10,542,893 B2  1/2020  LeBoeuf et al.
10,716,480 B2  7/2020  LeBoeuf et al.
(Continued)

FOREIGN PATENT DOCUMENTS

JP  63-61071 U  4/1988
JP  2008-233953 A  10/2008
(Continued)

OTHER PUBLICATIONS

Ashikur Rahman et al., "Doppler Radar Techniques for Accurate Respiration Characterization and Subject Identification", IEEE Journal on Emerging and Selected Topics in Circuits and Systems, vol. 8, No. 2, Jun. 2018, pp. 350-359.
(Continued)

*Primary Examiner* — Brian Werner
(74) *Attorney, Agent, or Firm* — Birch, Stewart, Kolasch & Birch, LLP

(57) ABSTRACT

A measurement unit (110) performs a measurement process for measuring a biological signal (21) from a target person (20). The biological signal (21) contains a plurality of components and can be measured in a manner to be unnoticeable by the target person (20). A component extraction unit (120) extracts an authentication component, which is to be used for authentication, from the plurality of components. A feature amount extraction unit (130) extracts a current feature amount indicating a present feature amount of the authentication component, from the authentication component. A registration unit (140) registers an identifier, which is used for identifying the target person (20), and a template feature amount, which is a feature amount extracted from the target person (20) in the past, in a storage unit (160), as template information (161). A comparison unit (150) compares the current feature amount to the template feature amount. When a difference between the current feature
(Continued)

amount and the template feature amount is within a tolerance value (162), the comparison unit (150) returns processing to the measurement process and the authentication is repeated. When the difference between the current feature amount and the template feature amount is larger than the tolerance value (162), the processing is ended.

6 Claims, 19 Drawing Sheets

(51) Int. Cl.
*G06V 40/12* (2022.01)
*G06V 40/13* (2022.01)
*G06V 40/10* (2022.01)
*G06V 40/50* (2022.01)
*A61B 5/0205* (2006.01)
*A61B 5/024* (2006.01)
*A61B 5/08* (2006.01)
*A61B 5/1172* (2016.01)

(52) U.S. Cl.
CPC .......... *A61B 5/0816* (2013.01); *A61B 5/1172* (2013.01); *G06V 40/1306* (2022.01); *G06V 40/1365* (2022.01); *G06V 40/15* (2022.01); *G06V 40/50* (2022.01)

(56) References Cited

U.S. PATENT DOCUMENTS

| | | | |
|---|---|---|---|
| 10,750,954 B2 | 8/2020 | LeBoeuf et al. | |
| 10,842,387 B2 | 11/2020 | LeBoeuf et al. | |
| 10,842,389 B2 | 11/2020 | LeBoeuf et al. | |
| 10,898,083 B2 | 1/2021 | LeBoeuf et al. | |
| 10,973,415 B2 | 4/2021 | LeBoeuf et al. | |
| 11,026,588 B2 | 6/2021 | LeBoeuf et al. | |
| 11,160,460 B2 | 11/2021 | LeBoeuf et al. | |
| 2010/0217100 A1 | 8/2010 | LeBoeuf et al. | |
| 2013/0131519 A1 | 5/2013 | LeBoeuf et al. | |
| 2013/0147972 A1* | 6/2013 | Niinuma | G06F 21/32 348/207.1 |
| 2014/0140567 A1 | 5/2014 | LeBoeuf et al. | |
| 2014/0249381 A1 | 9/2014 | LeBoeuf et al. | |
| 2014/0266696 A1* | 9/2014 | Addison | A61B 5/726 340/5.82 |
| 2014/0288394 A1 | 9/2014 | LeBoeuf et al. | |
| 2015/0080741 A1 | 3/2015 | LeBoeuf et al. | |
| 2015/0119657 A1 | 4/2015 | LeBoeuf et al. | |
| 2015/0135310 A1 | 5/2015 | Lee | |
| 2016/0183812 A1 | 6/2016 | Zhang et al. | |
| 2017/0011210 A1 | 1/2017 | Cheong et al. | |
| 2017/0188851 A1 | 7/2017 | LeBoeuf et al. | |
| 2017/0311840 A1 | 11/2017 | Suematsu et al. | |
| 2018/0000367 A1 | 1/2018 | Longinotti-Buitoni | |
| 2018/0106897 A1 | 4/2018 | Shouldice et al. | |
| 2018/0192950 A1 | 7/2018 | LeBoeuf et al. | |
| 2018/0228435 A1 | 8/2018 | LeBoeuf et al. | |
| 2018/0296166 A1 | 10/2018 | LeBoeuf et al. | |
| 2018/0317779 A1 | 11/2018 | Gregg et al. | |
| 2019/0099130 A1 | 4/2019 | LeBoeuf et al. | |
| 2019/0133474 A1 | 5/2019 | Longinotti-Buitoni | |
| 2019/0209045 A1 | 7/2019 | Gelissen et al. | |
| 2020/0386879 A1 | 12/2020 | Shouldice et al. | |
| 2021/0056289 A1 | 2/2021 | Kochi et al. | |
| 2021/0145290 A1 | 5/2021 | LeBoeuf et al. | |
| 2021/0353178 A1 | 11/2021 | Longinotti-Buitoni | |
| 2021/0393146 A1 | 12/2021 | LeBoeuf et al. | |
| 2022/0019763 A1 | 1/2022 | Kochi et al. | |
| 2022/0075050 A1 | 3/2022 | Shouldice et al. | |

FOREIGN PATENT DOCUMENTS

| | | | |
|---|---|---|---|
| JP | 2013-125341 A | 6/2013 | |
| JP | 2016-106734 A | 6/2016 | |
| JP | 2017-129981 A | 7/2017 | |
| JP | 2017-225834 A | 12/2017 | |
| JP | 2018-108467 A | 7/2018 | |
| JP | 2018-517448 A | 7/2018 | |
| JP | 2018-537163 A | 12/2018 | |
| JP | 2019-125002 A | 7/2019 | |
| JP | 2019-524204 A | 9/2019 | |
| JP | 2019-527603 A | 10/2019 | |
| WO | WO 2018/198286 A1 | 11/2018 | |

OTHER PUBLICATIONS

International Search Report for PCT/JP2020/000295 (PCT/ISA/210) dated Mar. 24, 2020.

Japanese Office Action dated Sep. 1, 2020 in the corresponding JP application No. 2020-537028 dated Sep. 1, 2020.

* cited by examiner

Fig. 2

161: TEMPLATE INFORMATION

| IDENTIFIER | MEASUREMENT DATE AND TIME | RESPIRATORY AMPLITUDE | RESPIRATORY RATE | ... |
|---|---|---|---|---|
| A | 2018/11/6 08:11:13 | 3.79 | 25 | ... |
| A | 2019/11/6 20:11:28 | 3.84 | 28 | ... |
| B | 2019/10/6 15:14:24 | 2.86 | 31 | ... |
| ... | ... | ... | ... | ... |

61 / 62 / 63: TEMPLATE FEATURE AMOUNT (631: RESPIRATORY AMPLITUDE, 632: RESPIRATORY RATE)

BIOMETRIC AUTHENTICATION DEVICE, BIOMETRIC AUTHENTICATION METHOD, AND COMPUTER READABLE MEDIUM

CROSS REFERENCE TO RELATED APPLICATION

This application is a Continuation of PCT International Application No. PCT/JP2020/000295, filed on Jan. 8, 2020, which is hereby expressly incorporated by reference into the present application.

TECHNICAL FIELD

The present disclosure relates to a biometric authentication device, a biometric authentication method, and a biometric authentication program.

BACKGROUND ART

There is an authentication method in which authentication is repeatedly performed after authentication is once performed. This authentication method is called continuous authentication. The continuous authentication is aimed to prevent replacement and impersonation of a target person after authentication.

Patent Literature 1 discloses the technique for continuously performing biometric authentication in a manner such that an ECG (Electrocardiogram) is measured and feature amounts are extracted from the electrocardiogram.

CITATION LIST

Patent Literature

Patent Literature 1: WO 2018/198286 pamphlet

SUMMARY OF INVENTION

Technical Problem

The continuous authentication is preferably performed while a target person is unaware of the authentication so as not to be noticed by an attacker and so as to reduce a burden on a user. The authentication method for authenticating a target person while the target person is unaware is called unnoticeable authentication. The ECG measurement disclosed in Patent Literature 1 sometimes requires a specific posture. Thus, the technique of Patent Literature 1 has a problem in that the unnoticeable authentication is difficult to be achieved.

An object of the present disclosure is to achieve continuous biometric authentication that is unnoticeable for a target person.

Solution to Problem

A biometric authentication device according to the present disclosure includes:

a measurement unit to perform a measurement process for measuring a biological signal from the target person of the authentication, the biological signal containing a plurality of components and being able to be measured in a manner to be unnoticeable by the target person;

a component extraction unit to extract a component, the component being to be used for the authentication, as an authentication component from the plurality of components;

a feature amount extraction unit to extract a current feature amount indicating a present feature amount, from the authentication component;

a registration unit to register an identifier and a template feature amount in a storage unit, as template information, the identifier being used for identifying the target person, the template feature amount being a feature amount extracted from the target person in a past; and a comparison unit to compare the current feature amount to the template feature amount registered in the template information so as to return processing to the measurement process and repeat the authentication when a difference between the current feature amount and the template feature amount is within a tolerance value, and so as to end the processing when the difference between the current feature amount and the template feature amount is larger than the tolerance value.

Advantageous Effects of Invention

The biometric authentication device according to the present disclosure achieves continuous biometric authentication that is unnoticeable for a target person, being able to detect replacement and impersonation of the target person.

BRIEF DESCRIPTION OF DRAWINGS

FIG. 2 is a drawing illustrating an example of template information according to Embodiment 1.

DESCRIPTION OF EMBODIMENTS

Figure 1:
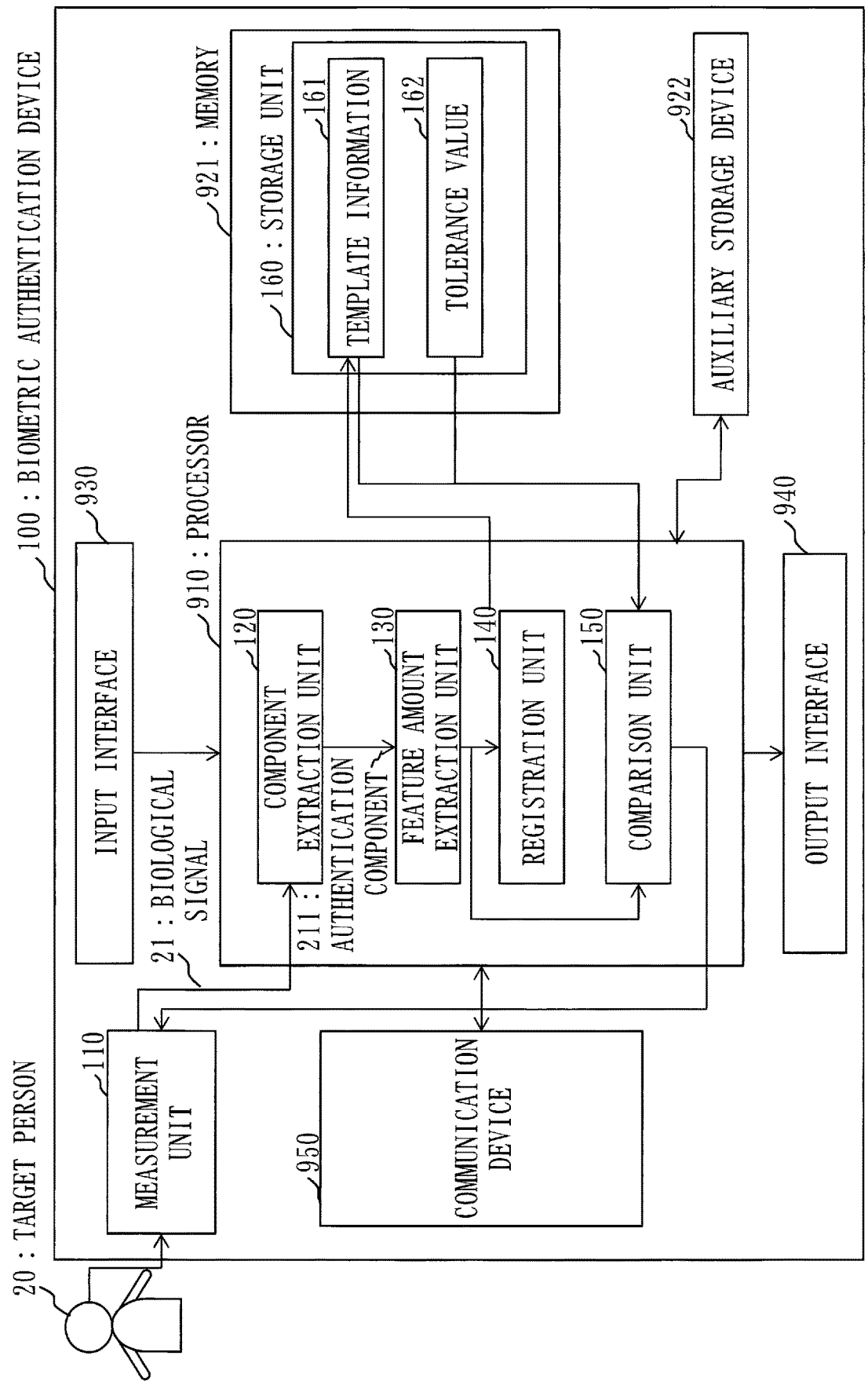
FIG. 1 is a configuration example of a biometric authentication device according to Embodiment 1.

Embodiments will be described below with reference to the accompanying drawings. The same or corresponding portions are given the same reference characters among the drawings. In the description of the embodiments, description will be omitted or simplified as appropriate for the same or corresponding portions. Further, in the following drawings, the relation between the sizes of components may differ from the actual relation. Further, in the description of the embodiments, orientations or positions such as top, bottom, left, right, forward, rearward, front, and back may be indicated. These notations are for convenience of explanation and do not limit the arrangement, directions, and orientations of devices, equipment, parts, or the like.

Embodiment 1

*Description on Configuration*

A configuration example of a biometric authentication device 100 according to the present embodiment will be described with reference to FIG. 1.

The biometric authentication device 100 is a computer. The biometric authentication device 100 includes a processor 910 and other pieces of hardware such as a memory 921, an auxiliary storage device 922, an input interface 930, an output interface 940, and a communication device 950. The processor 910 is connected with the other pieces of hardware via signal lines and control these other pieces of hardware.

A measurement unit 110 is a device for measuring a biological signal 21 from a target person 20 of authentication. The biometric authentication device 100 includes the measurement unit 110, a component extraction unit 120, a feature amount extraction unit 130, a registration unit 140, a comparison unit 150, and a storage unit 160 as functional elements. The storage unit 160 stores template information 161 and a tolerance value 162.

The functions of the component extraction unit 120, the feature amount extraction unit 130, the registration unit 140, and the comparison unit 150 are realized by software. The storage unit 160 is included in the memory 921. However, the storage unit 160 may be included in the auxiliary storage device 922 or included in the memory 921 and the auxiliary storage device 922 in a distributed manner.

The processor 910 is a device that executes a biometric authentication program. The biometric authentication program is a program for realizing the functions of the component extraction unit 120, the feature amount extraction unit 130, the registration unit 140, and the comparison unit 150. The biometric authentication program also includes a program that is executed when the measurement unit 110 realizes the function for measuring the biological signal 21 from the target person 20.

The processor 910 is an IC (Integrated Circuit) for performing arithmetic processing. Specific examples of the processor 910 include a CPU (Central Processing Unit), a DSP (Digital Signal Processor), and a GPU (Graphics Processing Unit).

The memory 921 is a storage device for temporarily storing data. A specific example of the memory 921 is a SRAM (Static Random Access Memory) or a DRAM (Dynamic Random Access Memory).

The auxiliary storage device 922 is a storage device for storing data. A specific example of the auxiliary storage device 922 is an HDD. Further, the auxiliary storage device 922 may be a portable storage medium such as an SD (registered trademark) memory card, a CF card, a NAND flash card, a flexible disk, an optical disk, a compact disk, a Blu-ray (registered trademark) disk, and a DVD. Here, HDD is an abbreviated word of Hard Disk Drive. SD (registered trademark) is an abbreviated word of Secure Digital. CF is an abbreviated word of CompactFlash (registered trademark). DVD is an abbreviated word of Digital Versatile Disk.

The input interface 930 is a port that is connected with an input device such as a mouse, a keyboard, and a touch panel. The input interface 930 is specifically a USB (Universal Serial Bus) terminal. Here, the input interface 930 may be a port that is connected with a LAN (Local Area Network).

Further, the input interface 930 may be connected with the measurement unit 110. The input interface 930 may serve as a sensor interface for acquiring the biological signal 21 of the target person 20 acquired by the measurement unit 110. FIG. 1 illustrates a single piece of input interface 930, but a plurality of input interfaces 930 may be provided.

The output interface 940 is a port to which a cable of an output device such as a display is connected. The output interface 940 is specifically a USB terminal or an HDMI (registered trademark) (High Definition Multimedia Interface) terminal. The display is specifically an LCD (Liquid Crystal Display). The output interface 940 is also referred to as a display interface.

The communication device 950 includes a receiver and a transmitter. The communication device 950 is connected with a communication network such as a LAN, Internet, and a telephone line. The communication device 950 is specifically a communication chip or a NIC (Network Interface Card). Here, the communication device 950 may serve as a communication interface for wirelessly acquiring the biological signal 21 of the target person 20 acquired by the measurement unit 110.

The biometric authentication program is executed in the biometric authentication device 100. The biometric authentication program is read in the processor 910 and executed by the processor 910. The memory 921 stores an OS (Operating System) as well as the biometric authentication program. The processor 910 executes the biometric authentication program while executing the OS. The biometric authentication program and the OS may be stored in the auxiliary storage device 922. The biometric authentication program and the OS stored in the auxiliary storage device 922 are loaded on the memory 921 and executed by the processor 910. Here, part or the whole of the biometric authentication program may be incorporated in the OS.

The biometric authentication device 100 may include a plurality of processors substituting for the processor 910. The plurality of processors share the execution of the biometric authentication program. Each of the processors is a device that executes the biometric authentication program as the processor 910.

Data, information, a signal value, and a variable value that are used, processed, or outputted by the biometric authentication program are stored in the memory 921, the auxiliary storage device 922, or a register or cache memory in the processor 910.

The "unit" of each of the measurement unit 110, the component extraction unit 120, the feature amount extraction unit 130, the registration unit 140, and the comparison unit 150 may be read as "process", "procedure", or "step". The biometric authentication program causes a computer to execute a measurement process, a component extraction process, a feature amount extraction process, a registration process, and a comparison process. The "process" of the measurement process, the component extraction process, the feature amount extraction process, the registration process, and the comparison process may be read as "program", "program product", "computer-readable storage medium that stores a program", or "computer-readable recording medium on which a program is recorded". Further, the biometric authentication method is a method that is performed when the biometric authentication device 100 executes the biometric authentication program.

The biometric authentication program may be provided in a manner to be stored in a computer-readable recording medium. Also, the biometric authentication program may be provided as a program product.

\*\*\*Description on Operation\*\*\*

An operation of the biometric authentication device 100 according to the present embodiment will now be described. An operation procedure of the biometric authentication device 100 corresponds to the biometric authentication method. Also, a program for realizing the operation of the biometric authentication device 100 corresponds to the biometric authentication program.

<Registration Process for Template Information 161>

FIG. 2 is a drawing illustrating an example of the template information 161 according to the present embodiment.

In the template information 161, an identifier 61 and a template feature amount 63 are set. The identifier 61 is used for identifying the target person 20 and the template feature amount 63 is a feature amount extracted from the target person 20 in the past. In addition, measurement date and time 62 of the template feature amount 63 may be set in the template information 161. In FIG. 2, the template feature amount 63 such as a respiratory amplitude 631 and a respiratory rate 632 is set in the template information 161. The identifier 61 is specifically information with which the target person 20 can be uniquely identified, such as a name and the number of the target person 20.

The registration process for the template information 161 according to the present embodiment will be described with reference to FIG. 3.

The registration unit 140 registers information including the identifier 61, which is used for identifying the target person 20, and the template feature amount 63, which is a feature amount extracted from the target person 20 in the past, in the storage unit 160, as the template information 161. The specific description will be provided below.

In step S101, a device for measuring the biological signal 21 is activated. Alternatively, a device for measuring the biological signal 21 is worn by the target person 20. A specific example of the device worn by the target person 20 is a device having a form of a bangle or a ring.

<Measurement Process: Measurement Unit 110>

In step S102, the measurement unit 110 performs the measurement process for measuring the biological signal 21 from the target person 20 of authentication. The biological signal 21 contains a plurality of components and can be measured in a manner to be unnoticeable by the target person 20.

Specifically, the measurement unit 110 measures a photoelectric volume pulse wave signal of the target person 20 as the biological signal 21 by using the device activated or worn in step S101. A photoelectric volume pulse wave is called PPG (Photoplethysmogram).

PPG measurement irradiates blood vessels with light through a skin and acquires reflected or transmitted light as an electrical signal so as to measure behaviors of the blood vessels such as expansion/contraction and relaxation. A PPG is mainly used to measure a heart rate or a pulse rate based on the fact that a behavior of a blood vessel is derived from a heart rate. Further, it is known that a component, other than a heartbeat-derived component, associated with respiration or body movement is superimposed on the heartbeat-derived component in a PPG. Components other than a heartbeat-derived component are often removed from a PPG signal so as to accurately measure a heart rate or a pulse rate.

A PPG can be measured with a wearable sensor and can be measured in a non-contact manner with a camera. Thus, a PPG can be measured without limiting a position and a direction of the target person 20. Further, a PPG can be measured in a specific indoor environment. A PPG measurement function is sometimes incorporated in a device such as a smart watch so as to measure a heart rate or a pulse rate.

Figure 4:
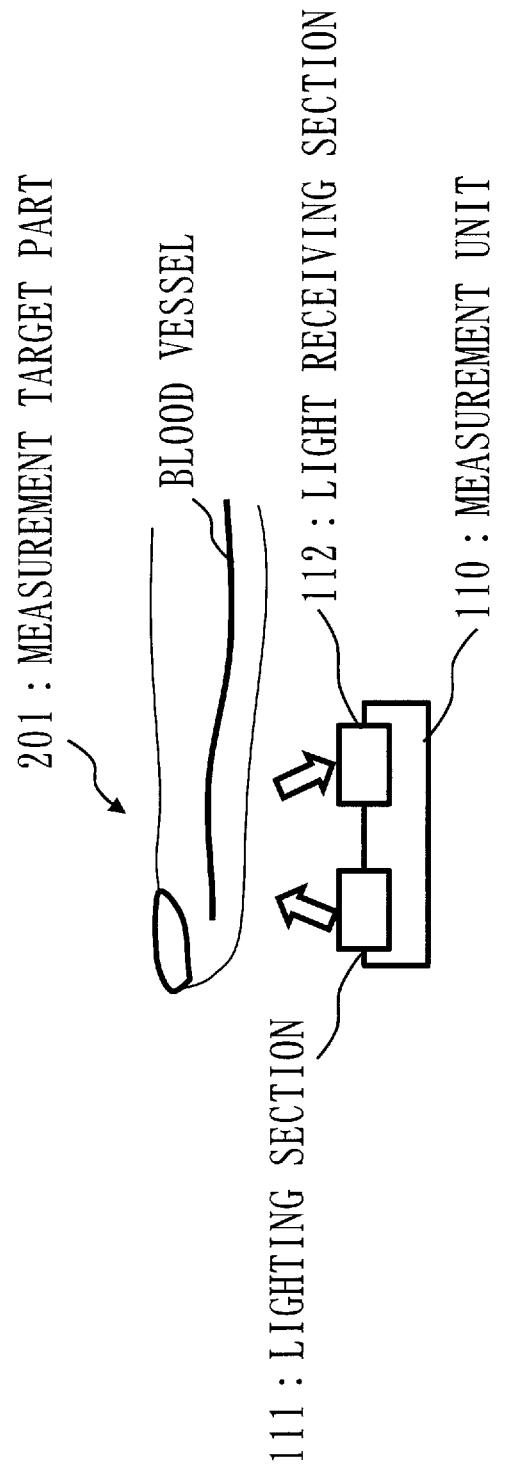
FIG. 4 is a drawing illustrating a mounting example of a measurement unit according to Embodiment 1.

FIG. 4 is a drawing illustrating a mounting example of the measurement unit 110 according to the present embodiment.

The measurement unit 110 is a sensor including a lighting section 111 and a light receiving section 112. The lighting section 111 is, for example, an LED (Light Emitting Diode). The light receiving section 112 is, for example, a photo diode. In the measurement unit 110 of FIG. 4, the lighting section 111 irradiates a skin with light and the light receiving section 112 acquires the reflected light or the transmitted light as an electrical signal. A measurement device for measuring a PPG generally measures a PPG from a measurement target part 201 such as a fingertip, an earlobe, and a wrist. However, other parts may be employed as a measurement part as long as a PPG can be measured from the parts.

The measurement unit 110 may be a device using a camera. The measurement unit 110 photographs a skin with the camera so as to measure a PPG in a non-contact manner.

Further, the measurement unit 110 may measure a PPG by combining a plurality of sensors and cameras. Furthermore, the measurement unit 110 may use other biological information measurement devices such as a respiratory rate monitor and an electrocardiogram monitor as well as sensors and cameras at the same time so as to enhance accuracy of a feature amount extracted by the feature amount extraction unit 130 which will be described later.

Alternatively, the measurement unit 110 may be a device that measures force (pressure) or displacement/deformation generated on a skin or a nail simultaneously with a PPG. Examples of the device include a strain gauge and a piezoelectric element, but other devices may be employed. Other sensors, cameras, and biological information measurement devices, including a PPG measurement device, may be simultaneously used.

<Component Extraction Process: Component Extraction Unit 120>

In step S103, the component extraction unit 120 extracts, from a plurality of components of the biological signal 21, a component, which is to be used for authentication, as an authentication component 211. As described above, the biological signal 21 contains a plurality of components such as a heartbeat-derived component and a component other than the heartbeat-derived component. For example, the component extraction unit 120 extracts, from a plurality of components of the biological signal 21, a component, which is a component other than a heartbeat-derived component and is derived from respiration of the target person 20, as the authentication component 211.

The component extraction unit 120 separates the biological signal 21 acquired by the measurement unit 110 into targeted components and inputs the components into the feature amount extraction unit 130. Examples of a separable component include a component based on behaviors in a body and human behaviors such as a heart rate, respiration, and body movement.

Figure 5:
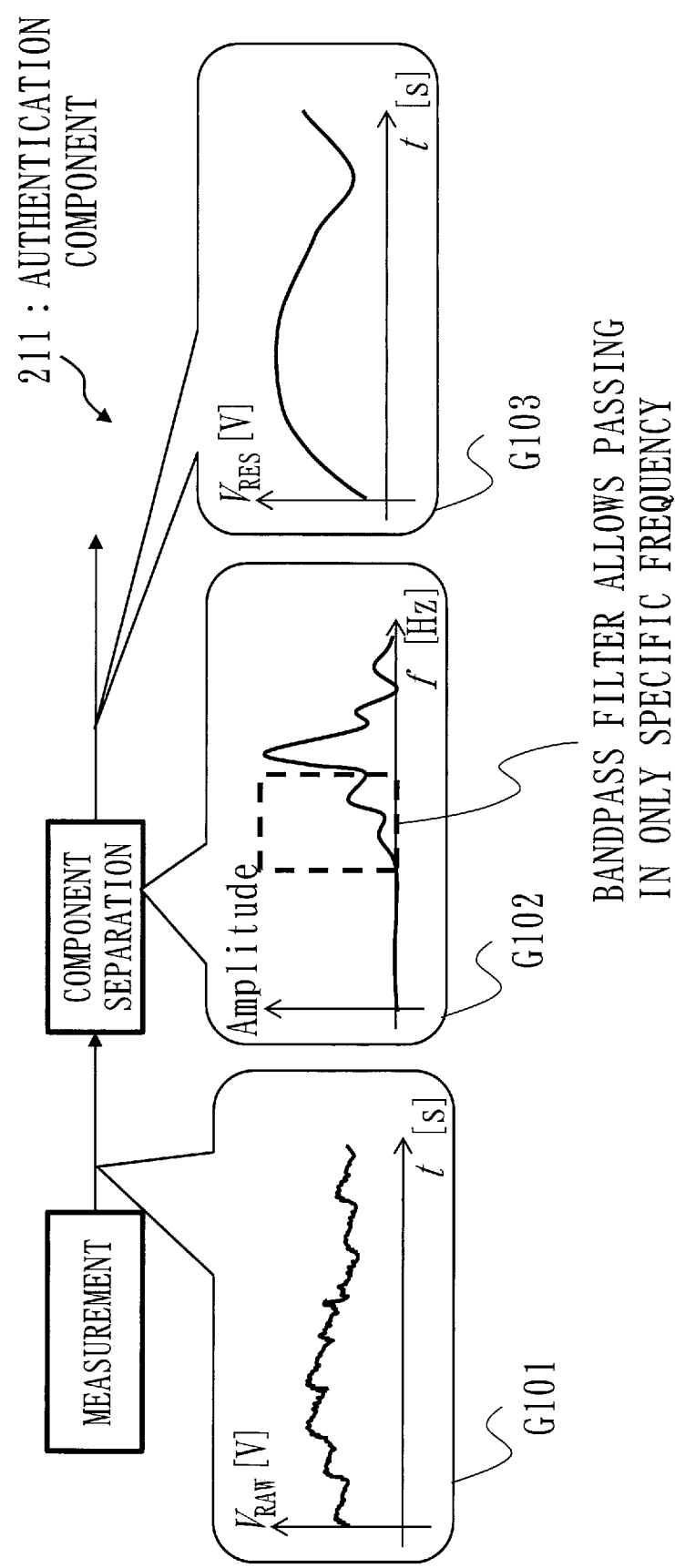
FIG. 5 is a drawing illustrating an example of component extraction according to Embodiment 1.

FIG. 5 is a drawing illustrating an example of component extraction according to the present embodiment.

Figure 6:
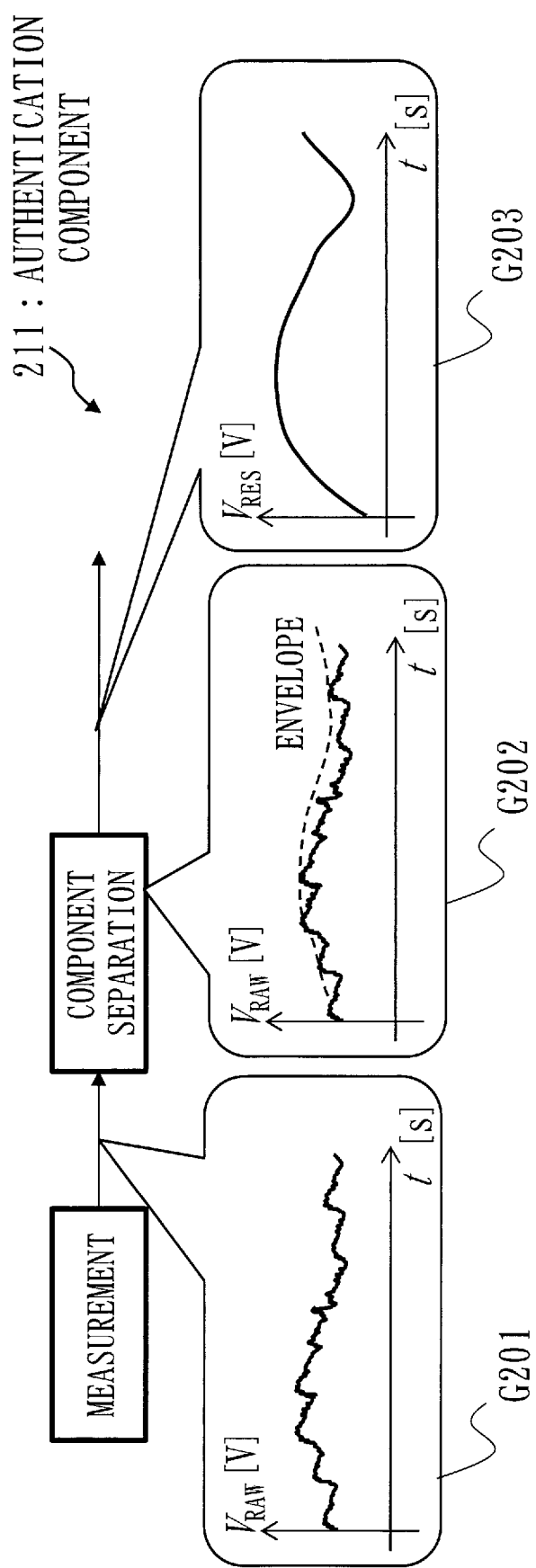
FIG. 6 is a drawing illustrating another example of component extraction according to Embodiment 1.

FIG. 6 is a drawing illustrating another example of component extraction according to the present embodiment.

In the present embodiment, the component extraction unit 120 extracts a component that is contained in a PPG and is derived from respiratory movement, as the authentication component 211. The component derived from respiratory movement is referred to as a respiration component below.

As a method for separating or extracting a component, there is a method for processing the biological signal 21 with an analog filter composed of an electric or electronic circuit. There also is a method for processing the biological signal 21 with a digital filter composed of a PC (Personal Computer) or a microcontroller. However, any method may be employed as long as a component can be separated or extracted from the biological signal 21 by the method.

For example, there is a method using a bandpass filter or the like so as to allow only components in a specific frequency domain to pass through and acquire the components, as illustrated in G102 of FIG. 5. Alternatively, there is an acquisition method based on an envelope of a PPG signal, as illustrated in G202 of FIG. 6.

<Feature Amount Extraction Process: Feature Amount Extraction Unit 130>

In step S104, the feature amount extraction unit 130 extracts a current feature amount indicating a present feature amount of the authentication component 211, from the authentication component 211.

Figure 7:
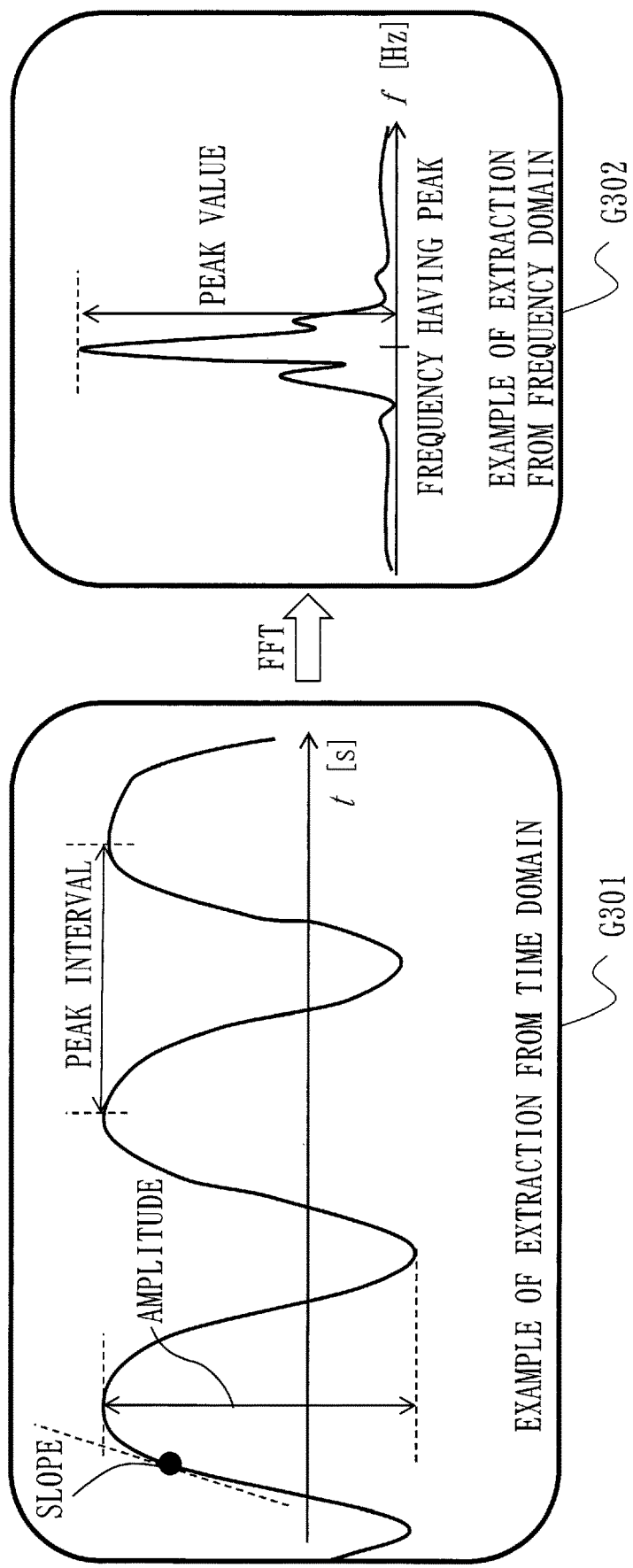
FIG. 7 is a drawing illustrating an example of feature amount extraction according to Embodiment 1.

FIG. 7 is a drawing illustrating an example of feature amount extraction according to the present embodiment.

The feature amount extraction unit 130 is capable of extracting a feature amount such as an amplitude or a slope of a signal waveform, as illustrated in G301 of FIG. 7. However, as long as a feature of the authentication component 211 can be indicated, the content and the number of pieces of features are not limited. Further, instead of determining and extracting a certain point in a signal of the authentication component 211, the feature amount extraction unit 130 may extract a maximum value or a minimum value in a predetermined time interval. Also, instead of limiting to the extraction only from a time-series signal, the feature amount extraction unit 130 may extract a feature amount from a waveform obtained by applying Fourier transform to a signal as illustrated in G302 in FIG. 7. In addition, the feature amount extraction unit 130 may extract a feature amount from a differentiated or integrated waveform.

<Registration Process. Registration Unit 140>

In step S105, the registration unit 140 registers a current feature amount, which is extracted by the feature amount extraction unit 130, in the template information 161, as the template feature amount 63. The template information 161 is provided as a database holding feature amounts of multiple people. A file format may be a format of CSV (comma-separated values) or XML (Extensible Markup Language). Other formats may also be employed.

In the example of the template information 161 of FIG. 2, feature amounts extracted from the authentication component 211 are held as the template feature amount 63 with respect to the identifier 61 for each target person 20. Further, the respiratory amplitude 631 and the respiratory rate 632 are held as the template feature amount 63.

Here, a plurality of sets of feature amounts may be held for a single identifier 61 through update of the template information 161. When a plurality of sets of feature amounts are held for a single identifier 61, the template information 161 needs to include an element with which the sets can be mutually distinguished, such as the measurement date and time 62.

In FIG. 2, two sets of feature amounts are held for the identifier 61 "A".

The registration process to the template information 161 is performed when measurement of the biological signal 21 is performed for the first time for the target person 20. Also, the registration process to the template information 161 may be performed every time measurement for the biological signal 21 is performed with respect to the target person 20, as Example 2 of the biometric authentication process described later.

Figure 8:
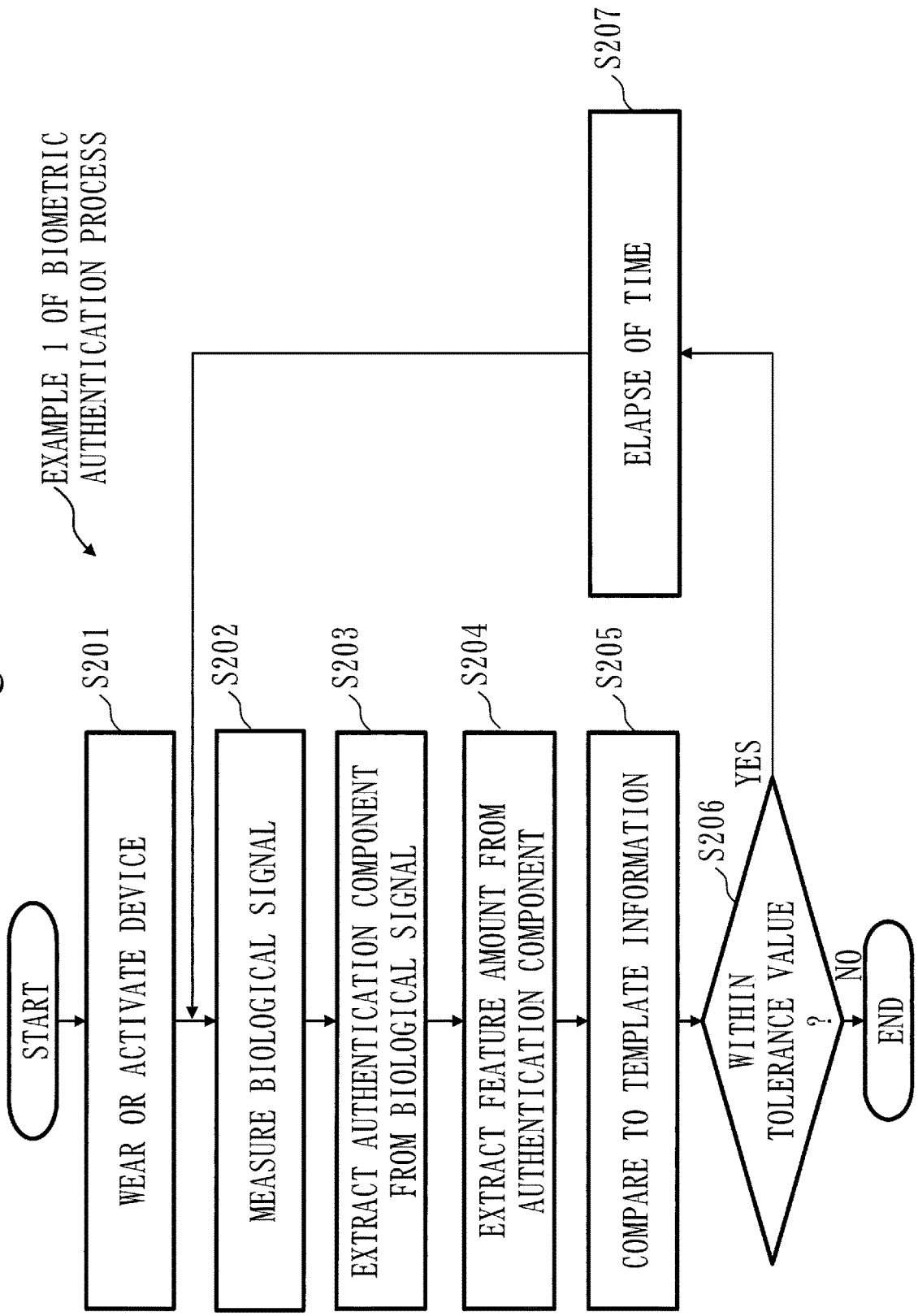
FIG. 8 is a flow diagram illustrating Example 1 of a biometric authentication process by the biometric authentication device according to Embodiment 1.

Example 1 of Biometric Authentication Process:
FIG. 8

Description will be provided on Example 1 of the biometric authentication process by the biometric authentication device 100 according to the present embodiment, with reference to FIG. 8.

Figure 3:
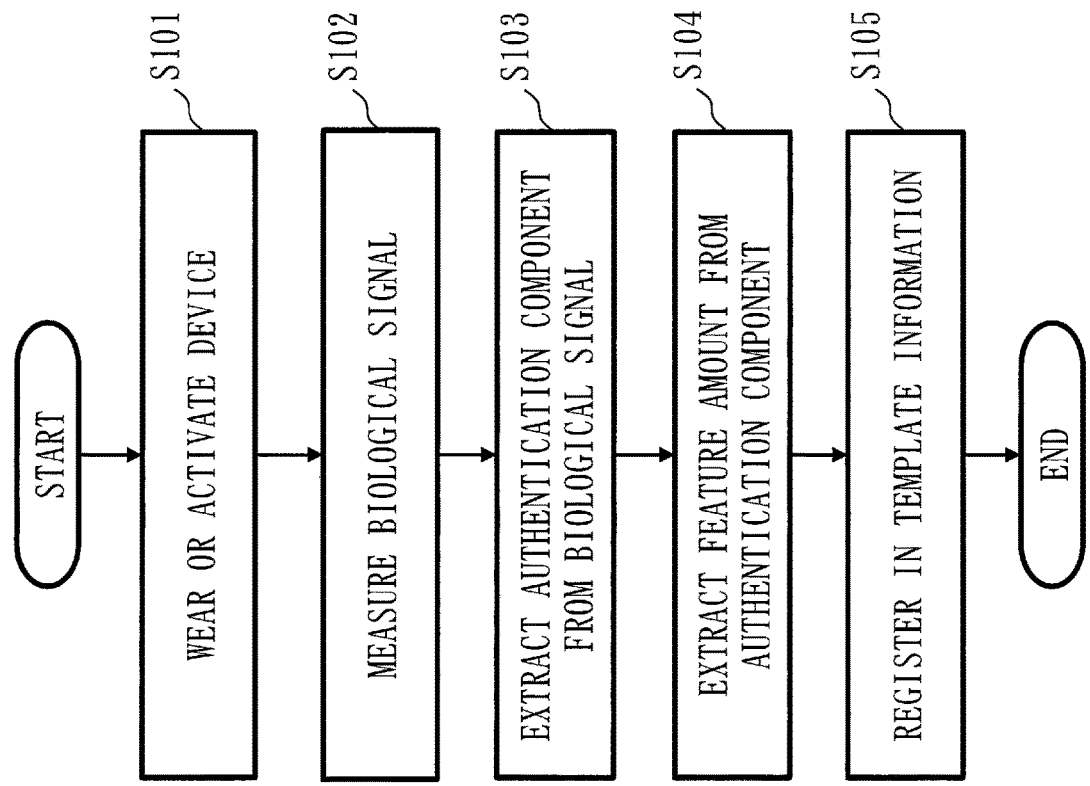
FIG. 3 is a flow diagram of a registration process for the template information according to Embodiment 1.

In FIG. 8, processing from step S201 to step S204 is the same as the processing from step S101 to step S104 described in FIG. 3. Through the processing from step S201 to step S204, a feature amount of the authentication component 211 is extracted as a current feature amount from a current biological signal 21 of the target person 20.

In step S205, the comparison unit 150 compares the current feature amount to the template feature amount 63 registered in the template information 161.

In step S206, the comparison unit 150 determines whether a difference between the current feature amount and the template feature amount 63 is within a tolerance value or not.

When the difference between the current feature amount and the template feature amount 63 is within the tolerance value, the comparison unit 150 returns the processing to the measurement process and authentication is repeated. The state in which the difference between the current feature amount and the template feature amount 63 is within the tolerance value means a state in which authentication to the target person 20 is successful. At this time, the biometric authentication device 100 may show information indicating the success of the authentication on a display thereof. The biometric authentication device 100 returns to the measurement process of step S202 after elapse of predetermined time from success in authentication for the target person 20 (step S207) and repeats the processing from step S201 to step S206 so as to perform continuous authentication. The elapse of time in step S207 may be elapse of a certain period of time or may be irregular.

When the difference between the current feature amount and the template feature amount 63 is larger than the tolerance value, the comparison unit 150 ends the processing. The state in which the difference between the current feature amount and the template feature amount 63 is larger than the tolerance value means a state in which authentication to the target person 20 is failed. At this time, the biometric authentication device 100 may show information indicating the failure of the authentication on the display thereof.

Example 1 of the biometric authentication process in FIG. 8 is the processing for comparing the latest current feature amount measured from the target person 20 with the template feature amount 63 which is unchanged since the initial registration every time.

However, after registration of the template feature amount 63, information such as a template feature amount used for authentication, a type of a feature amount used for comparison, and a tolerance value may be changed between the initial authentication and the second and subsequent authentication. This is because there is a possibility that authentication cannot be accurately performed due to change of a biological signal occurring when attributes such as a physical condition and movement of the target person 20 change after initial authentication.

The following description is about two types of authentication methods in which information used for comparison is changed between initial authentication and second and subsequent authentication. The first method is an authentication method in which a template feature amount is changed and the second method is an authentication method in which a type of a feature amount to be compared is changed.

In the following description, the initial authentication and the second and subsequent authentication will be described for the sake of clarity of description, but the following description is applicable to authentication up to the n-th (n: natural number) time and authentication on and after the (n+1)-th time. Further, two types of information are to be changed in the following description, but three or more types of information may be changed. An authentication method may be employed in which information to be compared is changed among the authentication up to the n-th time, the authentication on the (n+1)-th time, and authentication on and after the (n+2)-th time.

Figure 9:
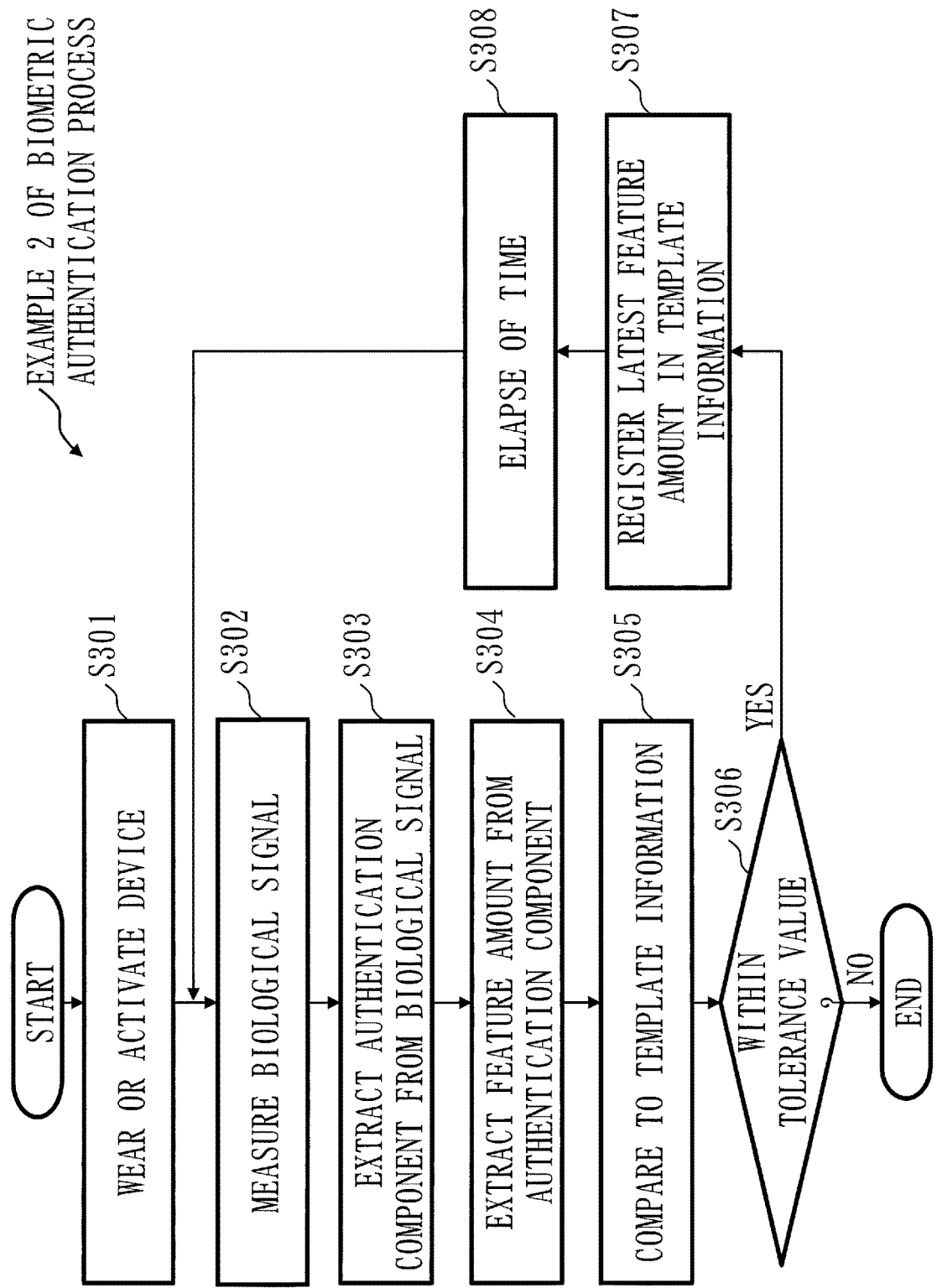
FIG. 9 is a flow diagram illustrating Example 2 of the biometric authentication process by the biometric authentication device according to Embodiment 1.

Example 2 of Biometric Authentication Process:
FIG. 9

Description will be provided on Example 2 of the biometric authentication process by the biometric authentication device 100 according to the present embodiment, with reference to FIG. 9.

In FIG. 9, processing from step S301 to step S306 and step S308 is the same as the processing from step S201 to step S207 described in FIG. 8.

When the difference between the current feature amount and the template feature amount 63 is within the tolerance value, the registration unit 140 registers the current feature amount as the template feature amount 63 in the template information 161 in step S307 before the processing returns to the measurement process. As illustrated in FIG. 2, the registration unit 140 may add the latest current feature amount of the target person 20 as the template feature amount 63 to the template information 161 together with the measurement date and time 62. Alternatively, the registration unit 140 may overwrite the latest current feature amount of the target person 20 on the template feature amount 63 of the target person 20.

Figure 10:
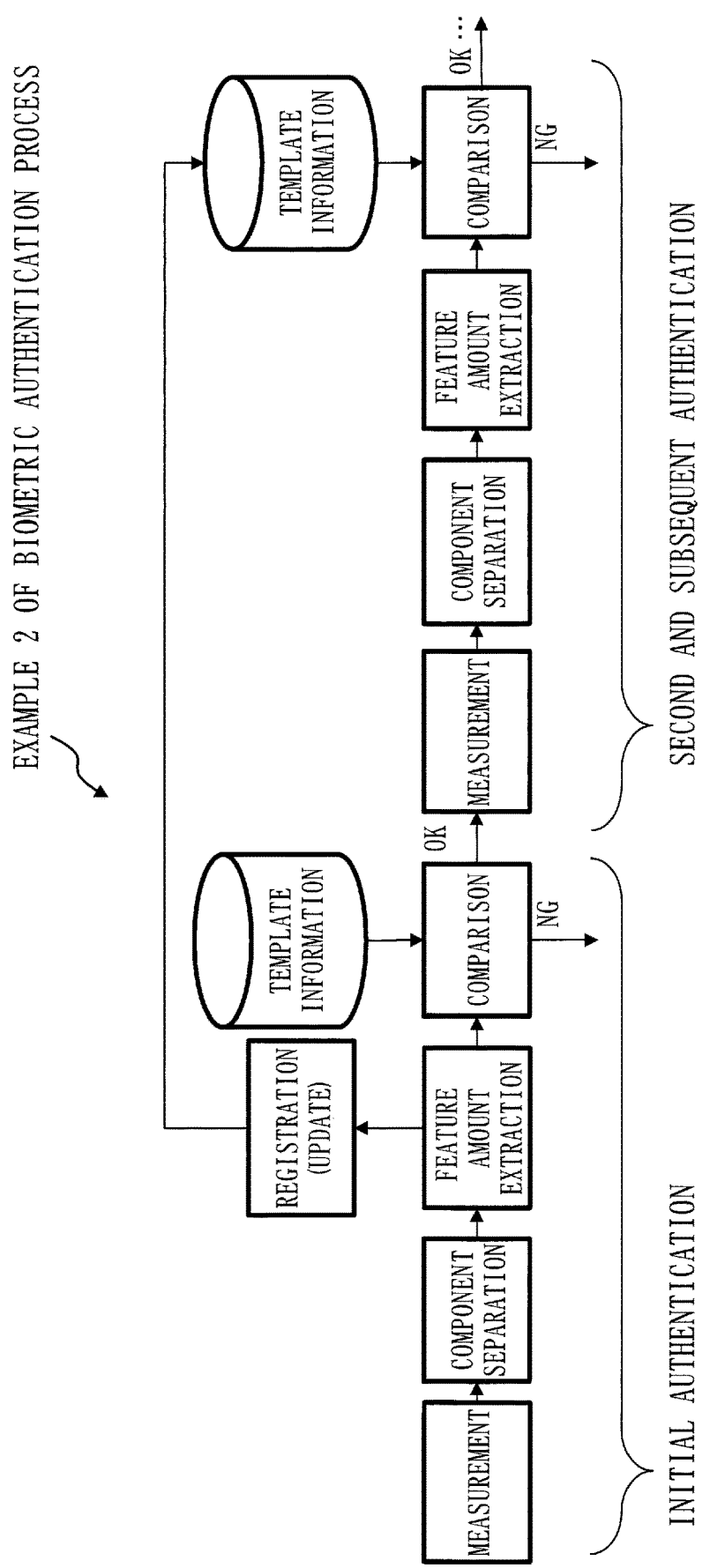
FIG. 10 is a schematic view illustrating Example 2 of the biometric authentication process by the biometric authentication device according to Embodiment 1.

FIG. 10 is a schematic view illustrating Example 2 of the biometric authentication process by the biometric authentication device 100 according to the present embodiment.

In Example 2 of the biometric authentication process illustrated in FIG. 10, the template information 161 is updated after the initial authentication and before the second authentication. The initial authentication uses the template information 161 which is initially registered, but the second and subsequent authentication uses a feature amount extracted in the initial authentication, as the template feature amount 63. When measurement from the same target person 20 is performed multiple times as the template information 161 of FIG. 2, the template feature amount 63 on the row including the latest measurement date and time 62 is used in the comparison.

Figure 11:
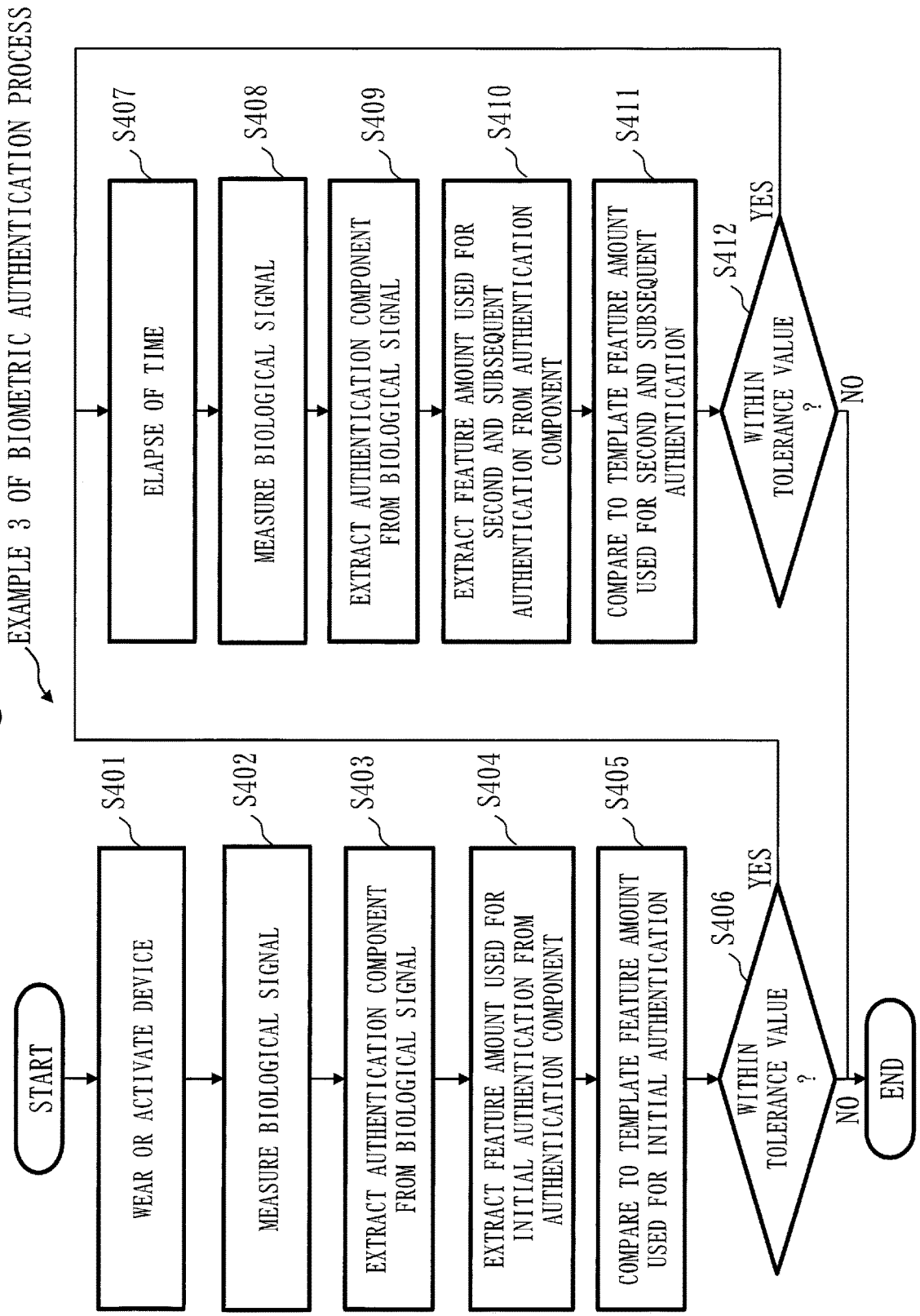
FIG. 11 is a flow diagram illustrating Example 3 of the biometric authentication process by the biometric authentication device according to Embodiment 1.

Example 3 of Biometric Authentication Process:
FIG. 11

Description will be provided on Example 3 of the biometric authentication process by the biometric authentication device 100 according to the present embodiment, with reference to FIG. 11.

In FIG. 11, processing from step S401 to step S407 is the same as the processing from step S201 to step S207 described in FIG. 8. Further, processing from step S408 to step S412 is the same as the processing from step S202 to step S206 described in FIG. 8.

However, the types of feature amounts extracted from the authentication component 211 and compared to the template information 161 are different from each other between steps S404, S405 and steps S410, S411.

The registration unit 140 registers a first template feature amount and a second template feature amount, whose type is different from that of the first template feature amount, in the template information 161, as the template feature amount 63.

In step S404, the feature amount extraction unit 130 extracts a first current feature amount, whose type is the same as that of the first template feature amount, as a current feature amount.

In step S406, the comparison unit 150 returns the processing to the measurement process when a difference between the first current feature amount and the first template feature amount is within a tolerance value. In this example, when the difference between the first current feature amount and the first template feature amount is within the tolerance value, the comparison unit 150 progresses the processing to the next measurement process after elapse of time (step S407 and step S408).

In step S410, the feature amount extraction unit 130 extracts a second current feature amount, whose type is the same as that of the second template feature amount, as a current feature amount.

Then, in step S411, the comparison unit 150 compares the second current feature amount to the second template feature amount. When a difference between the second current feature amount and the second template feature amount is within a tolerance value, the processing is returned to step S407 and the second and subsequent authentication process is repeated.

Figure 12:
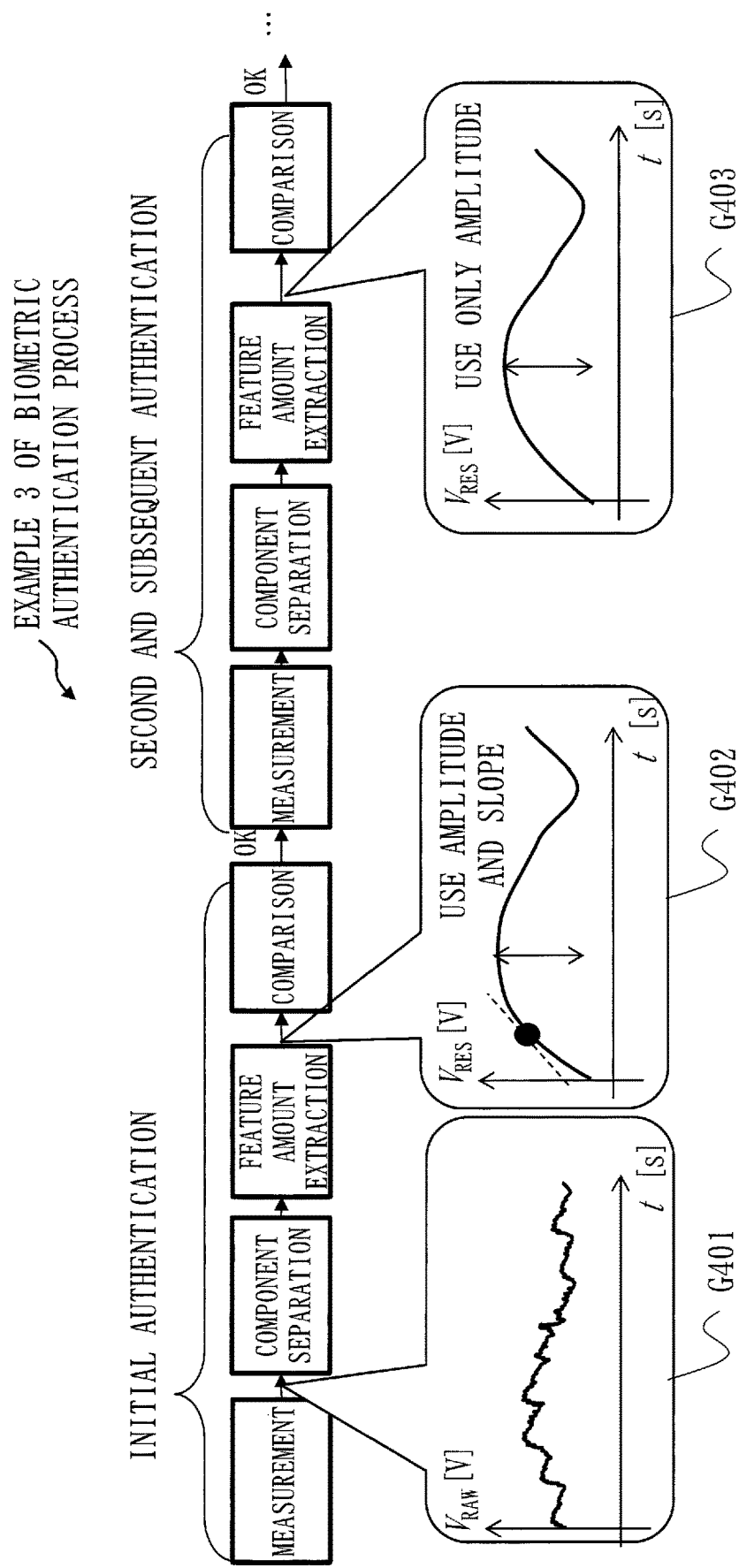
FIG. 12 is a schematic view illustrating Example 3 of the biometric authentication process by the biometric authentication device according to Embodiment 1.

FIG. 12 is a schematic view illustrating Example 3 of the biometric authentication process by the biometric authentication device 100 according to the present embodiment.

In Example 3 illustrated in FIG. 12, a feature amount is changed between the initial authentication and the second and subsequent authentication. In the initial authentication, an amplitude and a slope that are obtained from a biological signal G401 obtained in the initial measurement are used as feature amounts as illustrated in G402. Then, in the second and subsequent authentication, only an amplitude is used as a feature amount as illustrated in G403.

*Other Configurations*

The functions of the component extraction unit 120, the feature amount extraction unit 130, the registration unit 140, and the comparison unit 150 are realized by software in the present embodiment. As a modification, the functions of the component extraction unit 120, the feature amount extraction unit 130, the registration unit 140, and the comparison unit 150 may be realized by hardware.

Specifically, the biometric authentication device 100 is provided with an electronic circuit 909 instead of the processor 910.

Figure 13:
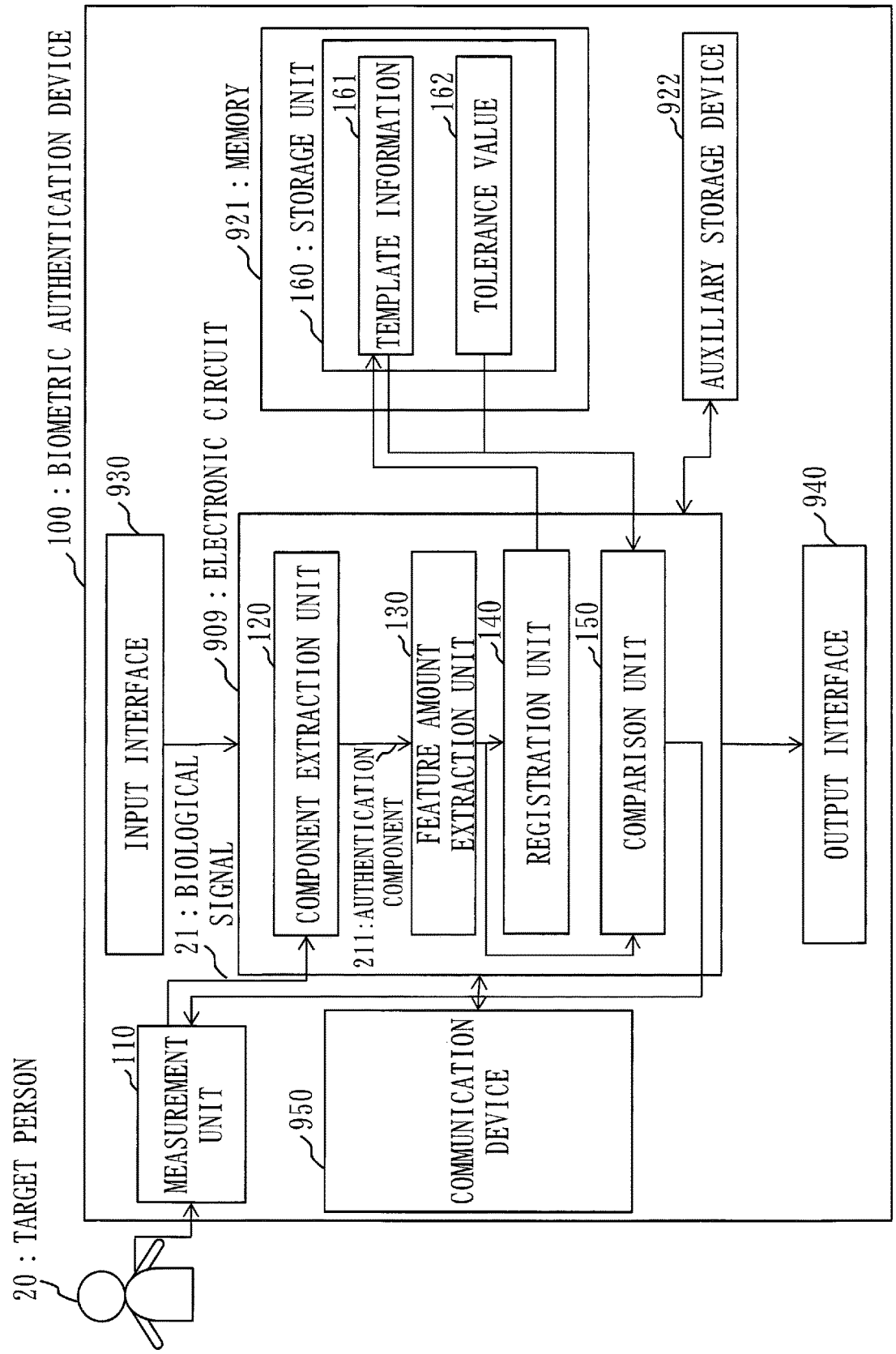
FIG. 13 is a configuration example of a biometric authentication device according to a modification of Embodiment 1.

FIG. 13 is a drawing illustrating a configuration of the biometric authentication device 100 according to a modification of the present embodiment.

The electronic circuit 909 is a dedicated electronic circuit for realizing the functions of the component extraction unit 120, the feature amount extraction unit 130, the registration unit 140, and the comparison unit 150. The electronic circuit 909 is, specifically, a single circuit, a composite circuit, a programmed processor, a parallel programmed processor, a logic IC, a GA, an ASIC, or an FPGA. GA is an abbreviated word of Gate Array. ASIC is an abbreviated word of Application Specific Integrated Circuit. FPGA is an abbreviated word of Field-Programmable Gate Array.

The functions of the component extraction unit 120, the feature amount extraction unit 130, the registration unit 140, and the comparison unit 150 may be realized by a single electronic circuit or may be realized in a manner to be distributed to a plurality of electronic circuits.

As another modification, part of the functions of the component extraction unit 120, the feature amount extraction unit 130, the registration unit 140, and the comparison unit 150 may be realized by an electronic circuit and the rest of the functions may be realized by software. Further, part or all of the functions of the component extraction unit 120, the feature amount extraction unit 130, the registration unit 140, and the comparison unit 150 may be realized by firmware.

Each of a processor and an electronic circuit is also called processing circuitry. That is, the functions of the component extraction unit 120, the feature amount extraction unit 130, the registration unit 140, and the comparison unit 150 are realized by processing circuitry.

*Description on Advantageous Effects of Present Embodiment*

As described above, the biometric authentication device 100 according to the present embodiment is capable of measuring a biological signal in an unnoticeable manner and extracting a feature amount, achieving continuous authentication. Thus, the biometric authentication device 100 according to the present embodiment is capable of performing unnoticeable and continuous authentication and detecting presence/absence of a target person and detecting replacement and impersonation of a target person.

Embodiment 2

In the present embodiment, points different from Embodiment 1 and points to be added to Embodiment 1 will be mainly described.

The present embodiment will provide the same reference characters to components having the same functions as those in Embodiment 1 and will omit the description thereof

*Description on Configuration*

Figure 14:
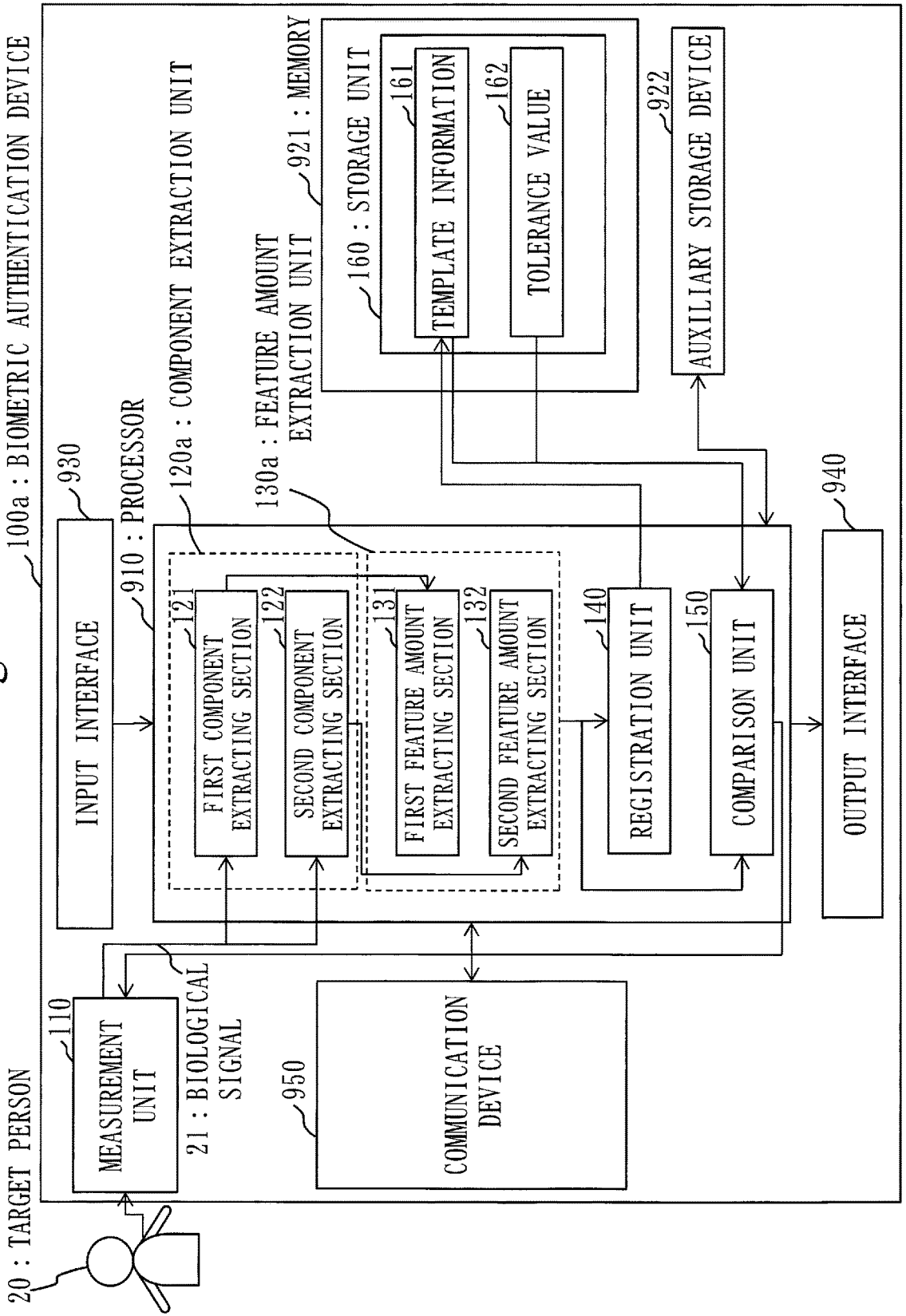
FIG. 14 is a configuration example of a biometric authentication device according to Embodiment 2.

A configuration example of a biometric authentication device 100a according to the present embodiment will be described with reference to FIG. 14.

A component extraction unit 120a and a feature amount extraction unit 130a of the present embodiment are different from Embodiment 1. The component extraction unit 120a includes a first component extracting section 121 and a second component extracting section 122. The feature amount extraction unit 130a includes a first feature amount extracting section 131 and a second feature amount extracting section 132.

Other configurations are the same as those of Embodiment 1.

The component extraction unit 120a extracts a plurality of authentication components as the authentication component 211, from a plurality of components of the biological signal 21. For example, the first component extracting section 121 extracts a respiration component as the authentication component 211, from the biological signal 21. Further, the second component extracting section 122 extracts a pulse component as the authentication component 211, from the biological signal 21.

*Description on Operation*

Figure 15:
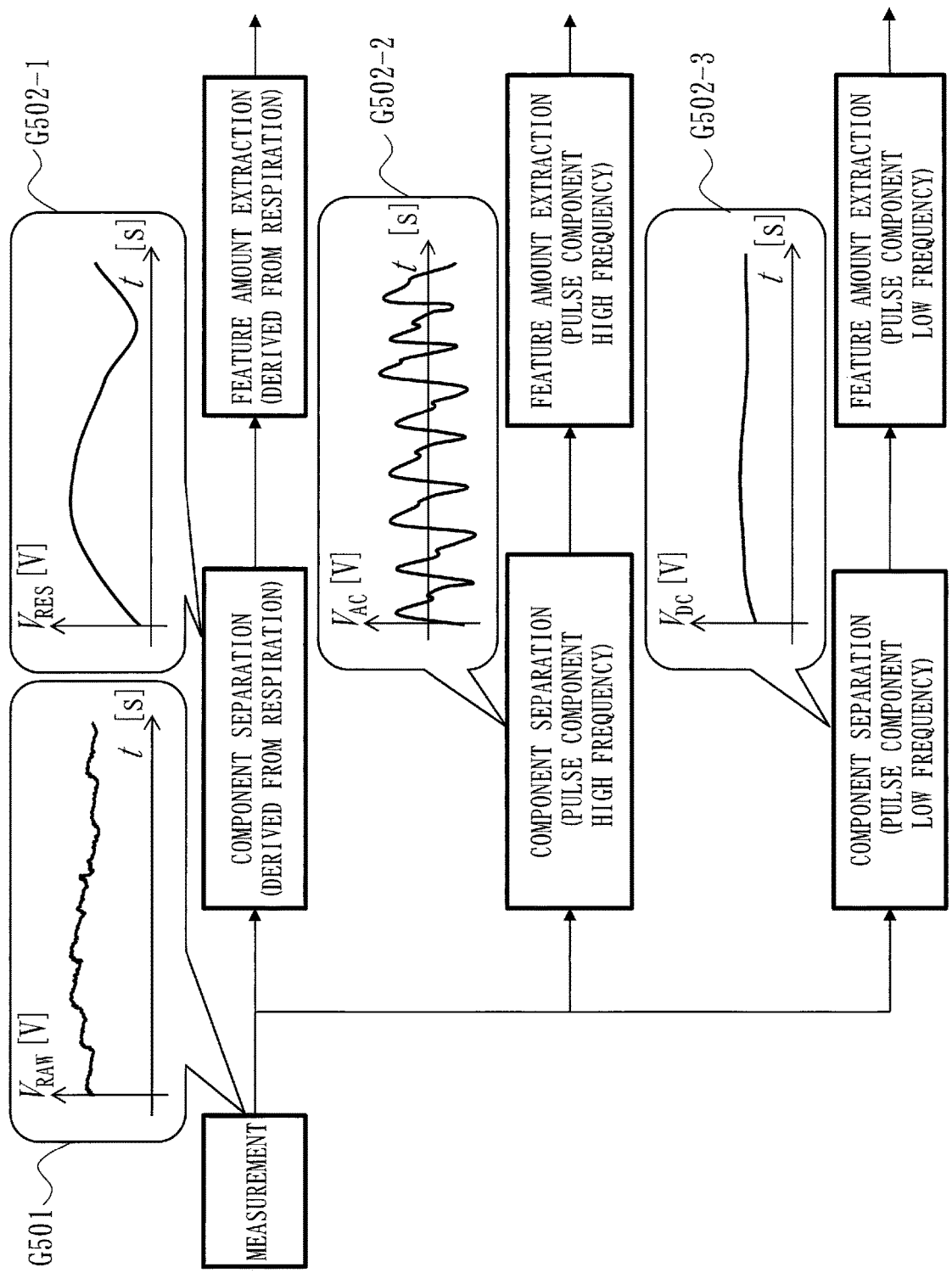
FIG. 15 is a drawing illustrating a component extraction example according to Embodiment 2.

FIG. 15 is a drawing illustrating a component extraction example according to the present embodiment.

In the present embodiment, the component extraction unit 120a separates a respiration component derived from respiratory movement and a pulse component derived from a pulse. The respiration component and the pulse component are contained in a PPG that is the biological signal 21. The component extraction unit 120a may further separate each component into a plurality of components. For example, a pulse component can be separated into a low frequency component and a high frequency component.

FIG. 15 illustrates an example in which a respiration component G502-1, a pulse component (high frequency component) G502-2, and a pulse component (low frequency component) G502-3, total three components, are separated from one PPG signal G501. Hereinafter, the present embodiment will describe a case of separation into two components that are a respiration component and a pulse component.

Subsequently, the feature amount extraction unit 130a extracts a current feature amount from each of a plurality of authentication components. For example, the first feature amount extracting section 131 extracts a feature amount from a respiration component acquired from the first component extracting section 121. Also, the second feature amount extracting section 132 extracts a feature amount from a pulse component acquired from the second component extracting section 122.

Figure 16:
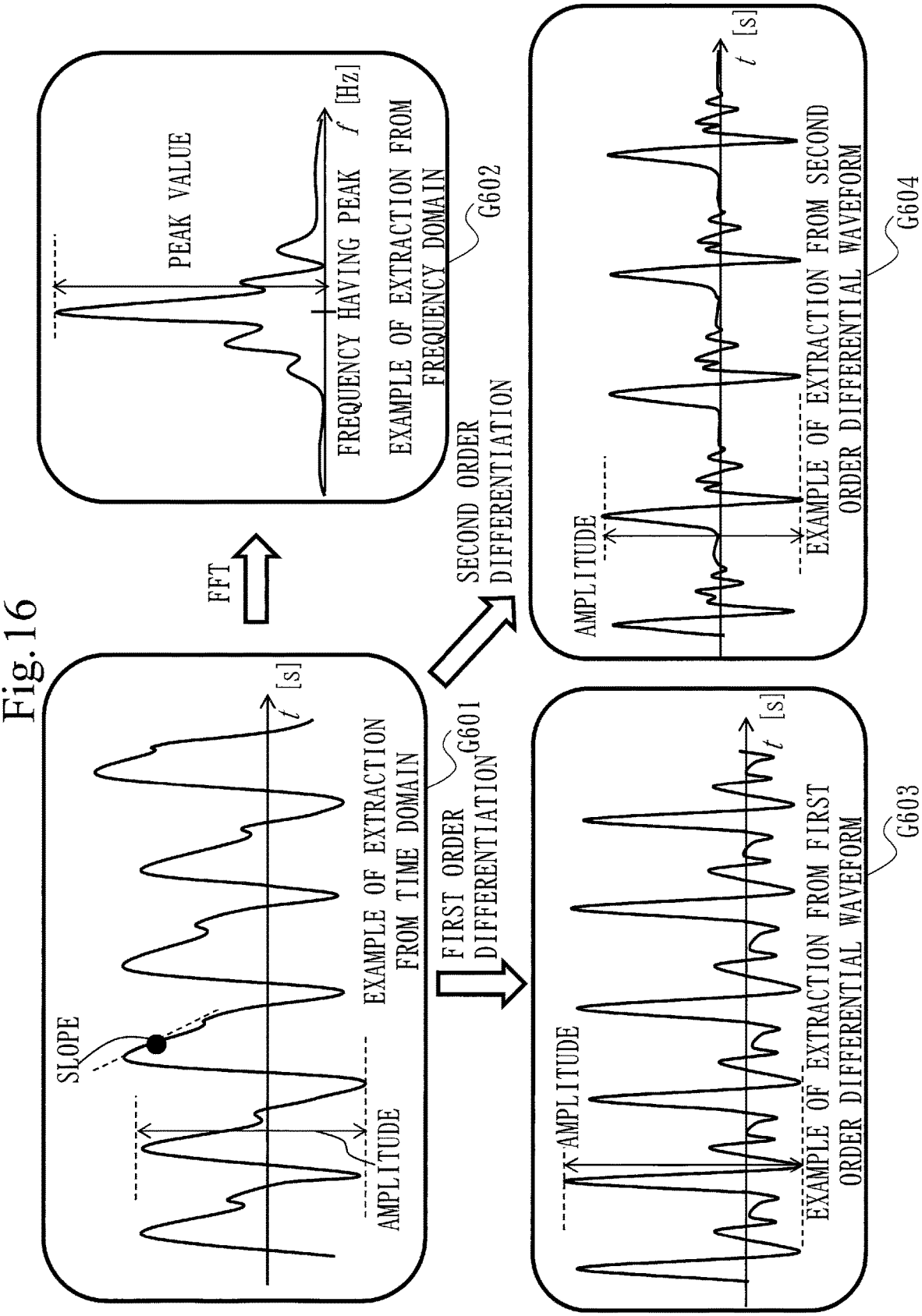
FIG. 16 is an example of extracting a feature amount from a pulse component according to Embodiment 2.

FIG. 16 is a drawing illustrating an example of extracting a feature amount from a pulse component according to the present embodiment.

The present embodiment does not limit contents or the number of pieces of extractable features either. The same type of feature amounts such as an amplitude and a slope may be extracted from all the components handled in the present embodiment, and a feature amount may be changed depending on a target component as both of an amplitude and a slope from a respiration component and only an amplitude from a pulse component.

Figure 17:
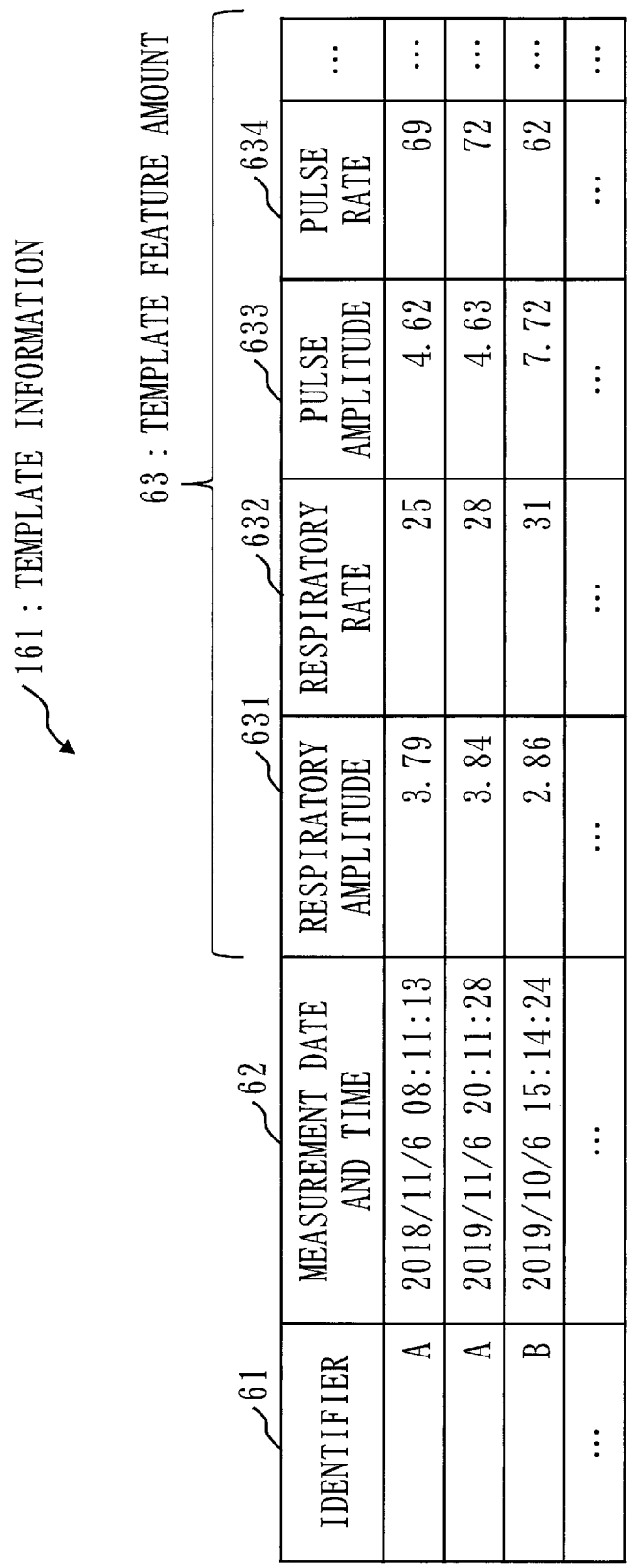
FIG. 17 is a drawing illustrating an example of template information according to Embodiment 2.

FIG. 17 is a drawing illustrating an example of the template information 161 according to the present embodiment.

When registration of a target person is performed after feature amounts are extracted, the registration unit 140 registers the feature amounts in the template information 161. Respective feature amounts extracted from separated components are held with respect to each user name or number. In FIG. 17, the respiratory amplitude 631, the respiratory rate 632, a pulse amplitude 633, and a pulse rate 634 are held as the template feature amount 63.

Figure 18:
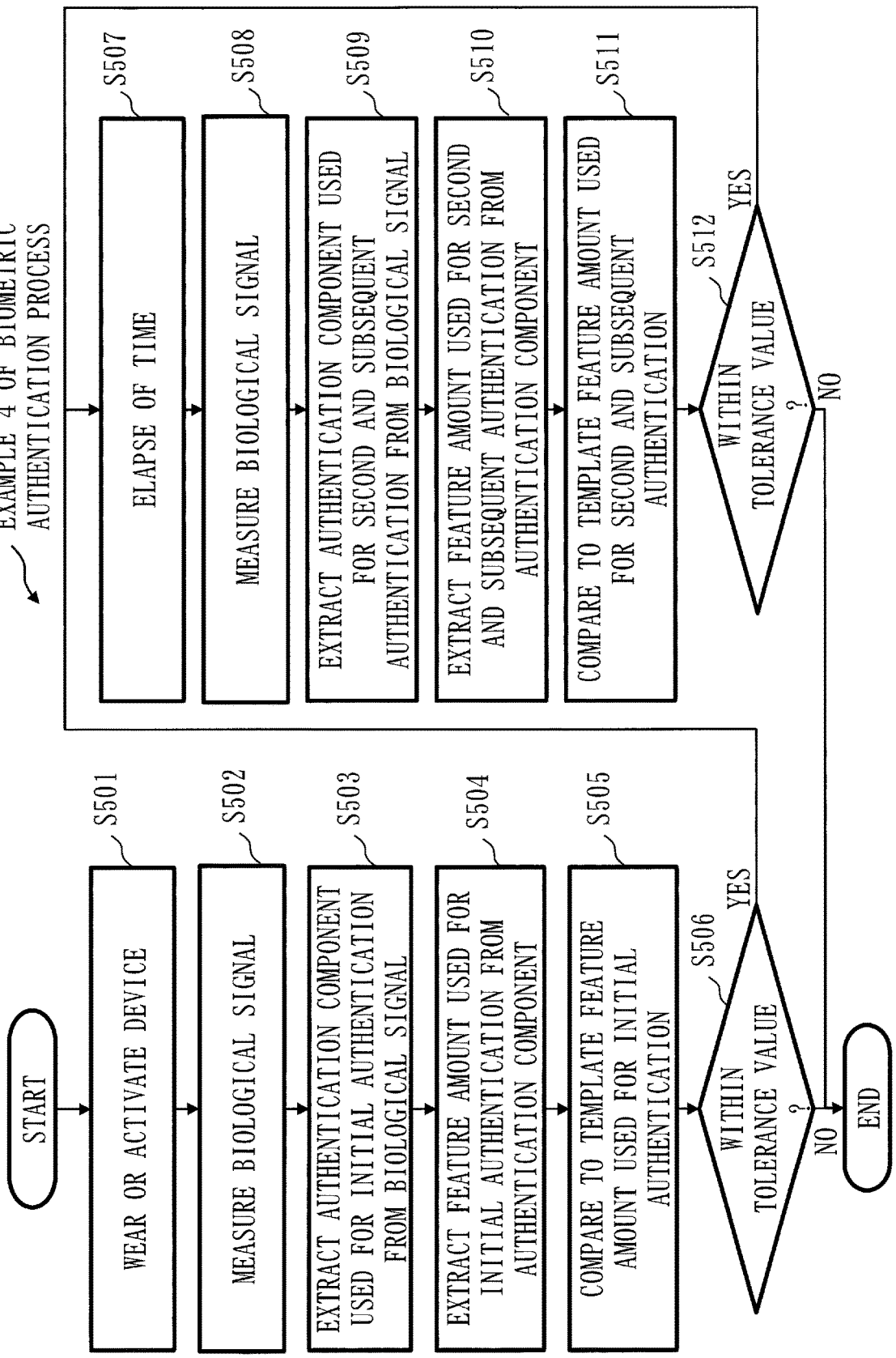
FIG. 18 is a flow diagram illustrating Example 4 of the biometric authentication process by the biometric authentication device according to Embodiment 2.

Description will be provided on Example 4 of the biometric authentication process by the biometric authentication device 100 according to the present embodiment, with reference to FIG. 18.

In FIG. 18, processing from step S501 to step S507 is the same as the processing from step S401 to step S407 described in FIG. 11. Further, processing from step S508 to step S512 is the same as the processing from step S408 to step S412 described in FIG. 11.

However, the types of authentication components extracted from the biological signal 21 are different from each other between step S503 and step S509. Also, the type of a feature amount extracted from each authentication component and compared to the template information 161 may be changed between steps S504, S505 and steps S510, S511.

Figure 19:
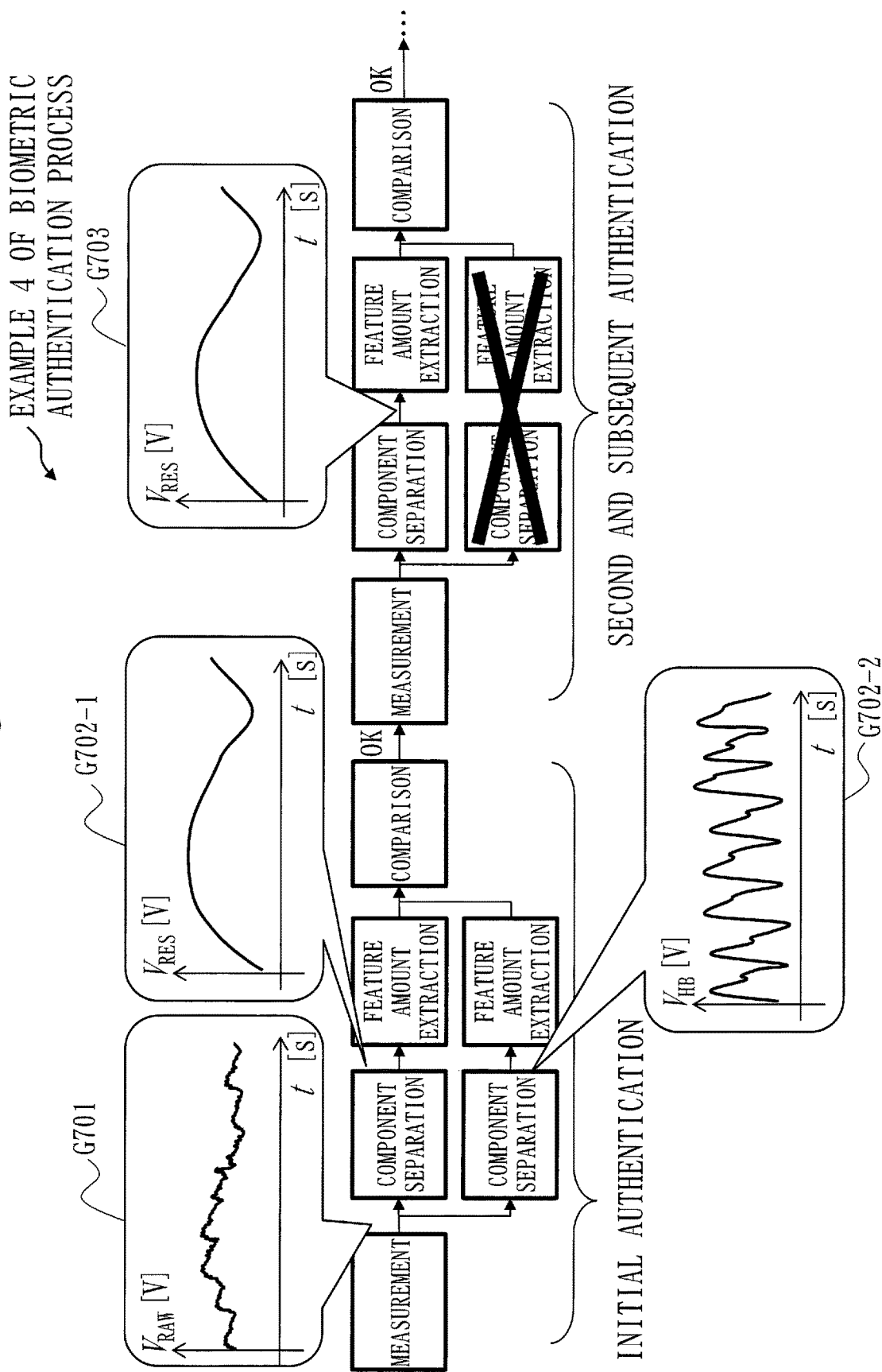
FIG. 19 is a schematic view illustrating Example 4 of the biometric authentication process by the biometric authentication device according to Embodiment 2.

FIG. 19 is a schematic view illustrating Example 4 of the biometric authentication process by the biometric authentication device 100 according to the present embodiment.

In Example 4 illustrated in FIG. 19, a target component, used for authentication, in a PPG signal is changed between the initial authentication and the second and subsequent authentication. In the initial authentication, both of a respiration component G702-1 and a pulse component G702-2 are separated and acquired from a measured PPG signal G701 and are used in the feature amount extraction unit and the comparison unit on later stages. After that, in the second and subsequent authentication, only a respiration component illustrated in G703 is used in the feature amount extraction unit and the comparison unit on later stages. Also, not limited to a signal component, a feature amount, a tolerance value, or the like may be changed as is the case with Embodiment 1.

*Other Configurations*

As is the case with Embodiment 1, the template information 161 may be updated between the initial authentication and the second and subsequent authentication also in the present embodiment. All feature amounts extracted from all authentication components may be updated or only part of authentication components or part of feature amounts may be updated in the present embodiment. For example, in the case of the template information 161 in FIG. 17, it is preferable to update both of the pulse amplitude 633 and the pulse rate 634 that are extracted from a pulse component derived from a heartbeat.

Description on Advantageous Effects of Present Embodiment

As described above, the biometric authentication device 100a according to the present embodiment is capable of performing unnoticeable and continuous authentication with higher accuracy. Thus, the biometric authentication device 100a according to the present embodiment is capable of detecting presence/absence of a target person and detecting replacement and impersonation of a target person with higher accuracy.

In Embodiments 1 and 2 above, each unit of the biometric authentication device is described as an independent functional block. However, the configuration of the biometric authentication device does not have to be as the configuration of the above-described embodiments. Any configuration may be employed as the functional block of the biometric authentication device as long as the function of the above-described embodiments can be realized with the configuration. Further, the biometric authentication device does not have to be a single device but may be a system composed of a plurality of devices.

Also, a plurality of parts in Embodiments 1 and 2 may be combined and carried out. Alternatively, one part in these embodiments may be carried out. In addition, these embodiments may be carried out in a manner to be entirely or partially combined in any way.

That is, in Embodiments 1 and 2, the embodiments can be freely combined, components of each embodiment can be arbitrarily transformed, or components in each embodiment can be arbitrarily omitted.

It should be noted that the embodiments described above are essentially preferred examples and are not intended to limit the scope of the present disclosure, the scope of the application of the present disclosure, and the scope of the uses of the present disclosure. The above-described embodiments can be variously modified as needed.

REFERENCE SIGNS LIST

20: target person; 21: biological signal; 211: authentication component; 100, 100a: biometric authentication device; 110: measurement unit; 111: lighting section; 112: light receiving section; 120, 120a: component extraction unit; 121: first component extracting section; 122: second component extracting section; 130, 130a: feature amount extraction unit; 131: first feature amount extracting section; 132: second feature amount extracting section; 140: registration unit; 150: comparison unit; 160: storage unit; 161: template information; 61: identifier; 62: measurement date and time; 63: template feature amount; 631: respiratory amplitude; 632: respiratory rate; 633: pulse amplitude; 634: pulse rate; 162: tolerance value; 201: measurement target part; 909: electronic circuit; 910: processor; 921: memory; 922: auxiliary storage device; 930: input interface; 940: output interface; 950: communication device

The invention claimed is:

1. A biometric authentication device to execute authentication to a target person by biometric authentication, the biometric authentication device comprising:
processing circuitry to:
perform a measurement process for measuring a biological signal from the target person, the biological signal being able to be measured in a manner to be unnoticeable by the target person,
separate a respiration component derived from respiratory movement and a pulse component derived from a pulse, from the biological signal and extract the respiration component and the pulse component as a plurality of authentication components being to be used for authentication,
extract a current feature amount indicating a present feature amount of each of the plurality of authentication components, from each of the plurality of authentication components,
register an identifier and a template feature amount in a memory, as template information, the identifier being used for identifying the target person, the template feature amount being a feature amount extracted from the target person in a past, and
compare the current feature amount to the template feature amount registered in the template information so as to return processing to the measurement process and repeat authentication when a difference between the current feature amount and the template feature amount is within a tolerance value, and so as to end the processing when the difference between the current feature amount and the template feature amount is larger than the tolerance value, wherein the processing circuitry executes authentication by using a current feature amount of each of the respiration component and the pulse component in initial authentication, and executes authentication by using a current feature amount of only the respiration component in second and subsequent authentication.

2. The biometric authentication device according to claim 1, wherein the processing circuitry measures a signal, the signal being derived from a behavior of a blood vessel of the target person, as the biological signal.

3. The biometric authentication device according to claim 1, wherein the processing circuitry registers the current feature amount in the template information, as the template feature amount, before processing returns to the measurement process when the difference between the current feature amount and the template feature amount is within the tolerance value.

4. The biometric authentication device according to claim 2, wherein the processing circuitry registers the current feature amount in the template information, as the template feature amount, before processing returns to the measurement process when the difference between the current feature amount and the template feature amount is within the tolerance value.

5. A biometric authentication method of a biometric authentication device to execute authentication to a target person by biometric authentication, the biometric authentication method comprising:

performing a measurement process for measuring a biological signal from the target person, the biological signal being able to be measured in a manner to be unnoticeable by the target person;

separating a respiration component derived from respiratory movement and a pulse component derived from a pulse, from the biological signal and extracting the respiration component and the pulse component as a plurality of authentication components being to be used for authentication;

extracting a current feature amount indicating a present feature amount of each of the plurality of authentication components, from each of the plurality of authentication components;

registering an identifier and a template feature amount in a memory, as template information, the identifier being used for identifying the target person, the template feature amount being a feature amount extracted from the target person in a past; and comparing the current feature amount to the template feature amount registered in the template information so as to return processing to the measurement process and repeat authentication when a difference between the current feature amount and the template feature amount is within a tolerance value, and so as to end the processing when the difference between the current feature amount and the template feature amount is larger than the tolerance value, wherein authentication is executed by using a current feature amount of each of the respiration component and the pulse component in initial authentication, and authentication is executed by using a current feature amount of only the respiration component in second and subsequent authentication.

6. A non-transitory computer readable medium storing a biometric authentication program of a biometric authentication device, the biometric authentication device executing authentication to a target person by biometric authentication and being a computer, the biometric authentication program causing the biometric authentication device to execute:

a measurement process of performing a measurement process for measuring a biological signal from the target person, the biological signal being able to be measured in a manner to be unnoticeable by the target person;

a component extraction process of separating a respiration component derived from respiratory movement and a pulse component derived from a pulse, from the biological signal and extracting the respiration component and the pulse component as a plurality of authentication components being to be used for authentication;

a feature amount extraction process of extracting a current feature amount indicating a present feature amount of each of the plurality of authentication components, from each of the plurality of authentication components;

a registration process of registering an identifier and a template feature amount in a memory, as template information, the identifier being used for identifying the target person, the template feature amount being a feature amount extracted from the target person in a past; and a comparison process of comparing the current feature amount to the template feature amount registered in the template information so as to return processing to the measurement process and repeat authentication when a difference between the current feature amount and the template feature amount is within a tolerance value, and so as to end the processing when the difference between the current feature amount and the template feature amount is larger than the tolerance value, where authentication is executed by using a current feature amount of each of the respiration component and the pulse component in initial authentication, and authentication is executed by using a current feature amount of only the respiration component in second and subsequent authentication.

* * * * *